United States Patent
Huang et al.

(10) Patent No.: US 10,364,270 B2
(45) Date of Patent: Jul. 30, 2019

(54) EYE-CARE PEPTIDE, ITS COMPOSITION AND METHOD OF USING THE SAME

(71) Applicant: PRO SUNFUN BIOTECH RESEARCH AND DEVELOPMENT CO., LTD., Kaohsiung (TW)

(72) Inventors: Min-Chuan Huang, Taipei (TW); Syue-Ting Chen, Taipei (TW); Yu-Chun Liu, Taoyuan (TW)

(73) Assignee: PRO SUNFUN BIOTECH RESEARCH AND DEVELOPMMENT CO., LTD., Kaohsiung (TW)

( * ) Notice: Subject to any disclaimer, the term of this patent is extended or adjusted under 35 U.S.C. 154(b) by 0 days.

(21) Appl. No.: 15/722,522

(22) Filed: Oct. 2, 2017

(65) Prior Publication Data

US 2019/0100555 A1    Apr. 4, 2019

(51) Int. Cl.
| | | |
|---|---|---|
| A61K 38/08 | (2019.01) | |
| A61K 38/00 | (2006.01) | |
| C07K 7/06 | (2006.01) | |
| C07K 7/00 | (2006.01) | |
| A61P 27/02 | (2006.01) | |

(52) U.S. Cl.
CPC ............... *C07K 7/06* (2013.01); *A61P 27/02* (2018.01); *A61K 38/00* (2013.01)

(58) Field of Classification Search
CPC .......... A61K 38/08; A61K 38/00; C07K 7/06; C07K 7/00
USPC ................. 514/20.8, 21.7, 1.1; 530/329, 300
See application file for complete search history.

(56) References Cited

U.S. PATENT DOCUMENTS

| | | | | |
|---|---|---|---|---|
| 7,745,391 B2 * | 6/2010 | Mintz | ..................... | G06F 19/24 514/19.3 |
| 2007/0083334 A1 * | 4/2007 | Mintz | ..................... | G06F 19/24 702/19 |

OTHER PUBLICATIONS

A0A0G2Z4F6 from UniProt, pp. 1-5. Integrated into UniProtKB/TrEMBL on Sep. 16, 2015.*

* cited by examiner

*Primary Examiner* — Julie Ha
(74) *Attorney, Agent, or Firm* — Birch, Stewart, Kolasch & Birch, LLP

(57) ABSTRACT

Disclosed is related to a synthetic peptide consisting of an amino acid sequence of ArgAsnProLeuGluGluThr (SEQ ID NO: 1). Also provided are a pharmaceutical composition benefic to eye care or eye health comprising the peptide, and a method for wound healing using the peptide.

6 Claims, 3 Drawing Sheets

Specification includes a Sequence Listing.

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Arg Asn Pro Leu Glu Glu Thr
1               5
```

EYE-CARE PEPTIDE, ITS COMPOSITION AND METHOD OF USING THE SAME

FIELD OF THE INVENTION

The present invention relates generally to a peptide effective for keeping eye health, its composition and method of using the same.

REFERENCE TO SEQUENCE LISTING SUBMITTED VIA EFS-WEB

This includes an electronically submitted sequence listing in .txt format. The .txt file contains a sequence listing entitled "2017-12-27_Sequence-Listing_5992-0188PUS1" created on Dec. 27, 2017 and is 428 bytes in size. The sequence listing contained in this .txt file is part of the specification and is hereby incorporated by reference herein in its entirety.

BACKGROUND OF THE INVENTION

It cannot do without eyes to operate computer, watch television, read books and newspaper, drive vehicle and play chess. Recently, most people spend much time in watching videos through non-mobile or mobile devices, such televisions, computers, desktops, laptops, tablets, phones etc., to cause visual impairment or a series of symptom such as eye dryness, discomfort, irritation, burning, redness, excess tearing, blurred vision, eye fatigue, soreness, strain, fear light, myopia, myopic astigmatism.

To prevent from any damage in eyes, there are many methods as developed in different ways. For example, it is easy to palliate eyestrain in our life by sleeping, dozing, closing eyes, sports, music, looking far, massaging eyes, wearing sunglasses, taking vitamins, taking eye drops, and so on. There are other methods to reduce irritation of eyes.

In conformity with such need in eye health, medicament, such as vitamins or herbal medicines or combinations thereof, have been proposed. But up to now, the medicaments beneficial to eye health are uncertain.

It is still desired to find or develop a non-toxic, non-antigenic, inexpensive eye-care agent for eye health.

BRIEF SUMMARY OF THE INVENTION

It is unexpectedly found in the present invention that a peptide having the amino acid sequence of ArgAsnProLeuGluGluThr (SEQ ID NO: 1) has an effect in enhancing the migration of corneal epithelial cells, which is benefic to eye care or eye health.

Accordingly, the present invention provides in one aspect a synthetic peptide consisting of the amino acid sequence of SEQ ID NO: 1, which is also named as "Peptide No. 12" herein. The peptide provides an effect in enhancing the migration of corneal epithelial cells.

In another aspect, the present invention provides a composition or a pharmaceutical composition benefic to eye care or eye health, comprising an effective amount of the peptide of SEQ ID NO: 1 in an amount effective to enhance the migration of fibroblast cells, and a pharmaceutically acceptable carrier.

In one embodiment of the invention, the composition of the invention is formulated in a systemic or topical form. In one particular example, the composition is formulated in a topical form, such as eye drop.

In one further aspect, the present invention provides an eye-care method for preventing eye damage, which comprises administering to a subject in need thereof the peptide having the amino acid sequence of SEQ ID NO: 1 in an amount effective to enhance the migration of corneal epithelial cells in the subject.

In one embodiment of the method according to the invention, the peptide is topically administered to the subject.

It is to be understood that both the foregoing general description and the following description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 1B provides the results of the statistic analysis of migration for 24 hours (*: $P<0.05$).

FIG. 2B provides the results of the statistic analysis of migration for 48 hours (**: $P<0.01$).

DETAILED DESCRIPTION OF THE INVENTION

Figure 1A:
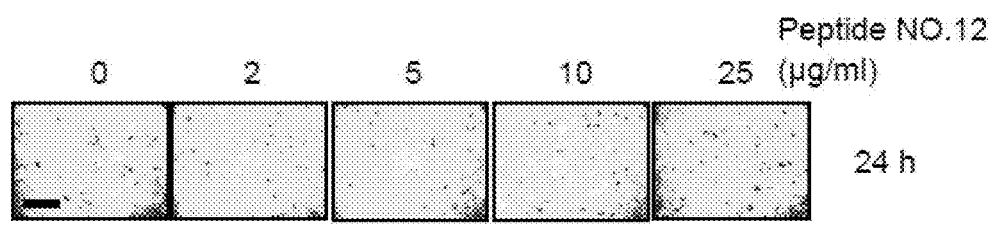
FIG. 1A and FIG. 1B show that Peptide NO. 12 enhanced migration of HCEC corneal epithelial cells for 24 hours; wherein FIG. 1A provides some representative images of cell migration for 24 hours analyzed by Transwell migration assay in HCEC cells treated with different concentrations of Peptide NO. 12 for 24 hours (Scale bar, 1 mm)
Figure 1B:
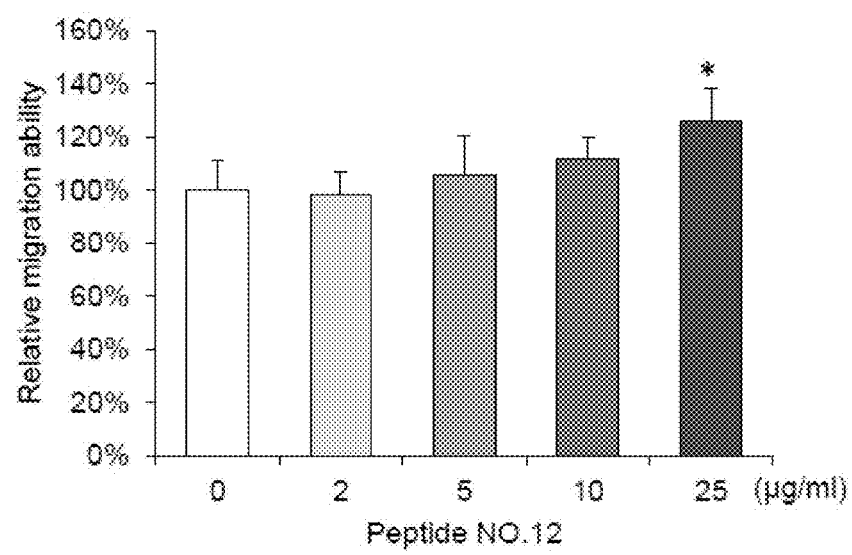
Figure 2A:
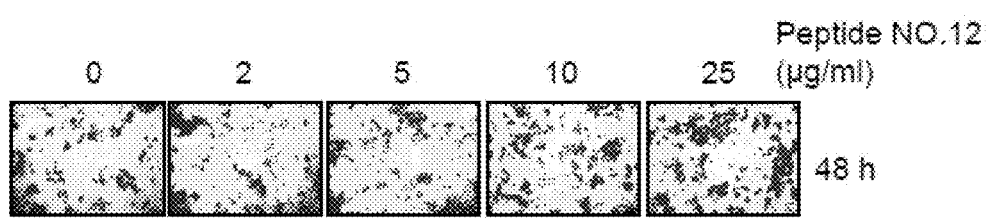
FIG. 2A and FIG. 2B show that Peptide NO. 12 enhanced migration of HCEC corneal epithelial cells for 48 hours; wherein FIG. 2A provides some representative images of cell migration in which the cells were treated with different concentrations of Peptide NO. 12 and analyzed by Transwell migration assay in HCEC cells for 48 hours (Scale bar, 1 mm)
Figure 2B:
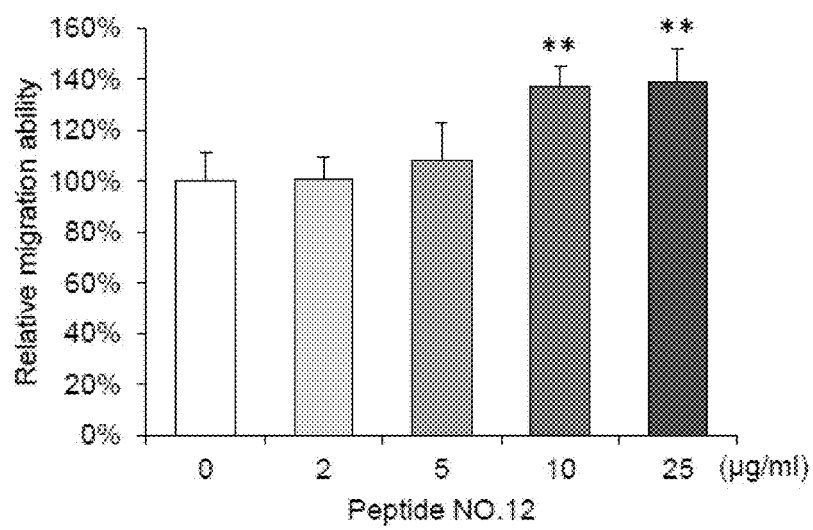

Unless defined otherwise, all technical and scientific terms used herein have the same meaning as commonly understood by those of ordinary skill in the art to which this invention belongs.

Unless defined otherwise, all technical and scientific terms used herein have the same meaning as commonly understood by those of ordinary skill in the art to which this invention belongs.

The use of the word "a" or "an" when used in conjunction with the term "comprising" in the claims and/or the specification may mean "one," but it is also consistent with the meaning of "one or more," "at least one," and "one or more than one."

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Standard abbreviations for amino acids are used.

As used herein, the term "subject" refers to a vertebrate or vertebrates, preferably mammals, including, for example, humans, laboratory animals such as rats and mice, and farm animals, such as horses and cows; particularly humans. Hereinafter, a human serving as a subject is specifically referred to as a "human subject."

As used herein, the term "carrier" or "cosmetically or pharmaceutically acceptable carrier" refers to any material commonly used on the formulations of cosmetic or pharmaceutical compositions used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "systemic" or "systemically" as used herein refers to a route of administration of medication or other substance into the circulatory system so that the entire body of a subject to be administered is affected. The administration may take place via enteral administration (through which the absorption of the medication or other substance through gastrointestinal tracts) or parenteral administration such as injection, infusion or implantation.

The term "topical" or "topically" is used herein its conventional sense as referring to a spot which can be in or on any part of the body, including but not limited to an eye or eyes, or any other part of the body. Topical administration or application means the direct contact of the peptide with tissue, such as a cornea.

The term "effective amount" as used herein refers to a sufficient amount of the peptide according to the invention to provide desired therapeutic or healthcare effects, or the induction of a particular type of response. The effective amount required varies from subject to subject, depending on the disease state, physical conditions, age, sex, species and weight of the subject, etc. However, an appropriate effective amount can be determined by one of ordinary skill in the art using only routine experimentation. For example, the peptide according to the invention may be administered systemically or topically.

The term "pharmaceutically acceptable carrier" as used herein encompasses any of the standard pharmaceutical carriers. Such carriers may include, but are not limited to: saline, buffered saline, dextrose, water, glycerol, ethanol, propylene glycol, cremophor, nanoparticles, liposome, polymer, and combinations thereof. In addition to standard carriers, a pharmaceutical composition of the present invention may be supplemented with one or more excipients that are normally employed in common standard formulations, such as surfactants, solubilizers, stabilizers, emulsifiers, thickeners, and preservatives. Such excipients are well known to those skilled in the art.

As shown in the examples, the peptide having the amino acid sequence of SEQ ID NO: 1, which may be artificially synthesized by a standard method or in any manner commonly used or known to one of ordinary skill. It was confirmed to have an effect in enhancing the migration of corneal epithelial cells, but not the growth of the cells. Therefore, the invention also provides a an eye-care method for preventing eye damage, which comprises administering to a subject in need thereof the peptide having the amino acid sequence of SEQ ID NO: 1 (also named as "Peptide No. 12) in an amount effective to enhance the migration of corneal epithelial cells in the subject.

On the other hand, the present invention provides the use of the peptide of the invention for manufacturing a pharmaceutical or healthcare composition benefic to eye care or eye health.

In addition, the invention provides a composition or a pharmaceutical composition benefic to eye care or eye health, comprising an effective amount of the peptide of SEQ ID NO: 1, and a pharmaceutically acceptable carrier.

The pharmaceutical composition of the present invention may be constituted with one or more pharmaceutically acceptable carriers into any form suitable for the mode of administration selected, including systemic and topical administrations via enteral or parenteral administration such as injection, infusion or implantation, oral, transdermal or topical administration. In certain embodiments of the invention, the composition may be formulated with a pharmaceutically or cosmetically acceptable carrier as a topical formulation in a solution, ointment, gel, serum, cream, lotion, powder, emulsion or any form for administration. In one particular example, the formulation may be administered in a form of eye drop.

The present invention is further illustrated by the following examples, which are provided for the purpose of demonstration rather than limitation.

EXAMPLES

Example 1: Preparation of Peptide No. 12

The peptide consisting of the sequence of ArgAsnPro-LeuGluGluThr (SEQ ID NO: 1) was synthesized by MDBio, Inc. (Taipei, Taiwan) and the purity and composition of peptide was confirmed by high performance liquid chromatography (HPLC) and mass spectrometry. Peptide stock was stored at −20'C after dissolving 10 mg of lyophilized peptide powder in 250 µl of double deionized water (dd $H_2O$).

Example 2: Efficacy Experiment

Materials and Method

Cell Culture

Human corneal epithelial cell line, HCEC, was cultured in complete KSF containing keratinocyte-serum free medium, 5 ng/ml human recombinant EGF, 0.05 mg/ml bovine pituitary extract, 0.005 mg/ml insulin and 500 ng/ml hydrocortisone under 5% $CO_2$ at 37° C.

Transwell Migration Assay

Cells ($3.5 \times 10^4$) in 0.25 ml keratinocyte-serum free medium were seeded into the upper chamber with an 8-µm pore size membrane (Corning, USA) and 0.5 ml 10% complete KSF with or without peptide NO. 12 were loaded to the lower chamber in 24-well culture plate. After 24-hour or 48-hour incubation, cells were fixed and stained with 0.5% (w/v) crystal violet (Sigma) containing 20% (v/v) methanol. The migrated cells from 5 random fields were counted under a phase-contrast microscope. Results obtained were analyzed by student's t-test and graphed as mean±SD.

MTT Assay

Cells ($2 \times 10^4$) in 1 ml complete KSF were seeded in 12-well plates with or without Peptide NO. 12. Seventy microliters of 5 mg/ml 3-(4,5-dimethyl-2-thiazolyl)-2,5-diphenyl-2H-tetrazolium bromide solution (MTT; Sigma) was added to each well for the indicated times and incubated at 37° C. for 3 hours, after which 700 µl 10% SDS in 0.01 N HCl was added to dissolve the MTT formazan crystals. The resultant optical density was measured spectrophotometrically at dual wavelengths, 550 and 630 nm.

Results

Figure 3:
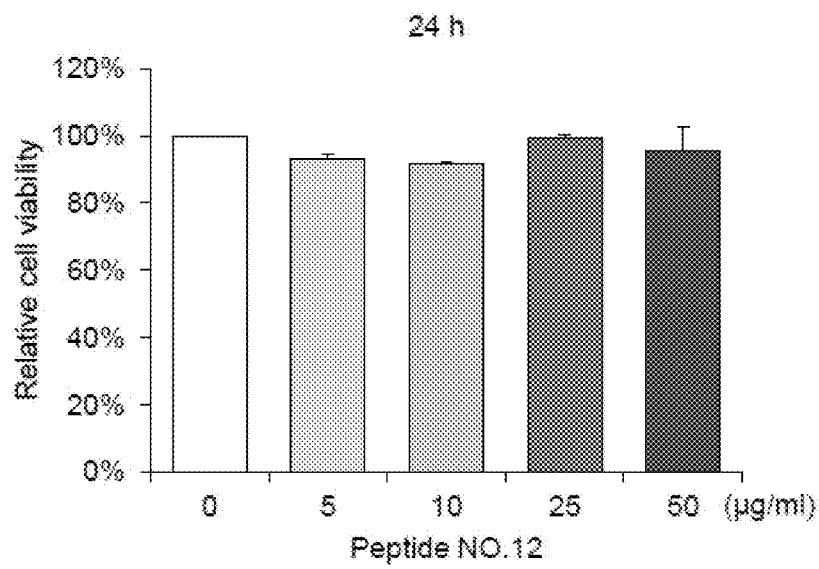
FIG. 3 shows that Peptide NO. 12 did not significantly affect viability of HCEC cells for 24 hours; wherein the HCEC cells were treated with different concentrations of Peptide NO. 12 for 24 hours and then analyzed by MTT assays.
Figure 4:
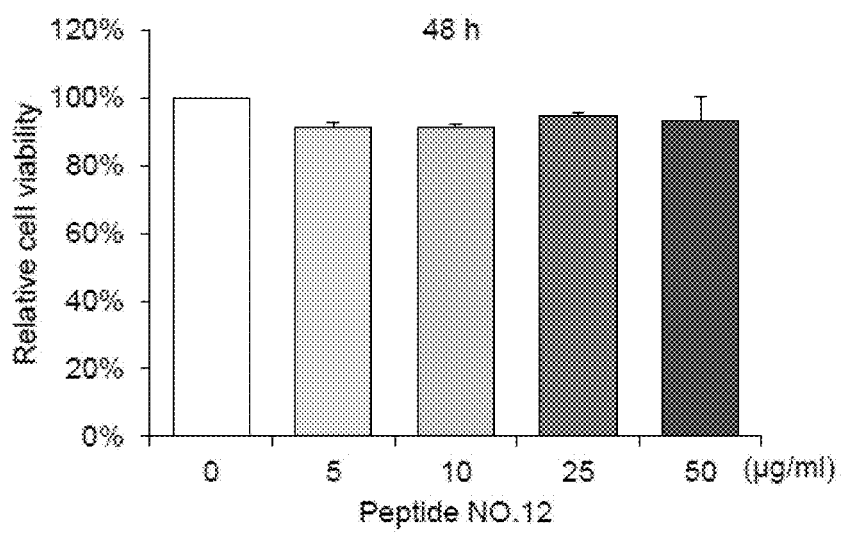
FIG. 4 shows that Peptide NO. 12 did not significantly affect viability of HCEC cells for 48 hours; wherein the HCEC cells were treated with different concentrations of Peptide NO. 12 for 48 hours and then analyzed by MTT assays.

The HCEC corneal epithelial cells were treated with 0, 2, 5, 10 and 25 µg/ml of Peptide NO. 12, for 24 and 48 hours respectively, and then was analyzed by transwell migration assay. As shown in FIGS. 1A, 1B, 2A and 2B, Peptide NO. 12 enhanced the migration of HCEC corneal epithelial cells. However, as shown in FIG. 3 and FIG. 4, Peptide NO. 12 in either of the concentrations of 5, 10, 25 and 50 µg/ml, did not significantly affect viability of HCEC cells for 24 and 48 hours, respectively.

Given the above, it is concluded that the peptide of SEQ ID NO: 1 provide an unexpected efficacy in the enhancement of the migration of migration of corneal epithelial cells, instead of the cell viability f corneal epithelial cells.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A pharmaceutical composition, comprising a peptide consisting of the amino acid sequence set forth in SEQ ID NO: 1 in an amount effective to enhance the migration of fibroblast cells, and a pharmaceutically acceptable carrier, wherein said pharmaceutical composition is formulated in a systemic or topical form.

2. The pharmaceutical composition of claim 1, which is formulated in a topical form.

3. The pharmaceutical composition of claim 1, which is in a form of eye drop.

4. An eye-care method for treating eye damage, which comprises
administering to a subject in need thereof the pharmaceutical composition of claim 1 in an amount effective to enhance the migration of corneal epithelial cells in the subject.

5. The method of claim 4, wherein the pharmaceutical composition is topically administered to the subject.

6. The method of claim 4, wherein the pharmaceutical composition is formulated in a form of eye drop.

* * * * *